United States Patent
Zuidema et al.

(10) Patent No.: US 10,953,392 B2
(45) Date of Patent: Mar. 23, 2021

(54) PROCESS FOR PREPARING A MOLYBDENUM-PLATINUM-BASED CATALYST FOR THE SYNTHESIS OF BENZENE BY TRANSALKYLATION

(71) Applicant: SHELL OIL COMPANY, Houston, TX (US)

(72) Inventors: Erik Zuidema, Amsterdam (NL); Ingrid Maria Van Vegchel, Amsterdam (NL); Daniël Banen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 16 days.

(21) Appl. No.: 16/467,615

(22) PCT Filed: Dec. 6, 2017

(86) PCT No.: PCT/EP2017/081673
§ 371 (c)(1),
(2) Date: Jun. 7, 2019

(87) PCT Pub. No.: WO2018/104382
PCT Pub. Date: Jun. 14, 2018

(65) Prior Publication Data
US 2019/0308176 A1 Oct. 10, 2019

(30) Foreign Application Priority Data

Dec. 8, 2016 (EP) ..................... 16203011

(51) Int. Cl.
| | |
|---|---|
| *B01J 29/80* | (2006.01) |
| *B01J 37/02* | (2006.01) |
| *B01J 37/08* | (2006.01) |
| *C07C 6/12* | (2006.01) |
| *B01J 35/00* | (2006.01) |
| *B01J 37/00* | (2006.01) |
| *B01J 29/22* | (2006.01) |
| *B01J 35/02* | (2006.01) |

(Continued)

(52) U.S. Cl.
CPC .............. *B01J 29/80* (2013.01); *B01J 29/22* (2013.01); *B01J 29/44* (2013.01); *B01J 35/002* (2013.01); *B01J 35/0006* (2013.01); *B01J 35/023* (2013.01); *B01J 37/0009* (2013.01); *B01J 37/0205* (2013.01); *B01J 37/08* (2013.01); *C07C 6/126* (2013.01); *C07C 15/04* (2013.01); *B01J 29/26* (2013.01); *B01J 29/48* (2013.01); *B01J 37/18* (2013.01); *B01J 2229/186* (2013.01); *B01J 2229/20* (2013.01); *B01J 2229/42* (2013.01); *C07C 2529/22* (2013.01); *C07C 2529/26* (2013.01); *C07C 2529/44* (2013.01); *C07C 2529/48* (2013.01); *C07C 2529/80* (2013.01)

(58) Field of Classification Search
CPC ... B01J 29/80; B01J 29/48; B01J 29/44; B01J 29/26; B01J 29/22; B01J 2229/20; B01J 2229/42; B01J 2229/186; B01J 37/08; B01J 37/0205; B01J 37/0009; B01J 37/04; B01J 35/002; B01J 35/0006; B01J 35/023; B01J 37/16; C07C 6/126; C07C 15/04; C07C 15/06; C07C 15/08; C07C 2529/22; C07C 2529/26; C07C 2529/44; C07C 2529/48; C07C 2529/80
USPC ........ 502/60, 63, 64, 66, 67, 69, 71, 74, 77, 502/78; 585/446, 467, 470, 475
See application file for complete search history.

(56) References Cited

U.S. PATENT DOCUMENTS

| | | |
|---|---|---|
| 3,702,886 A | 11/1972 | Argauer et al. |
| 4,511,547 A | 4/1985 | Iwayama et al. |
| 4,575,416 A | 3/1986 | Chester et al. |
| 5,041,401 A * | 8/1991 | Schoennagel .......... B01J 29/061 502/61 |

(Continued)

FOREIGN PATENT DOCUMENTS

| | | |
|---|---|---|
| EP | 1447131 A1 | 8/2004 |
| EP | 1730093 A1 | 12/2006 |

(Continued)

OTHER PUBLICATIONS

International Search Report and Written Opinion received for PCT Patent Application No. PCT/EP2017/081673 dated Mar. 29, 2018, 12 pages.

(Continued)

*Primary Examiner* — Elizabeth D Wood
(74) *Attorney, Agent, or Firm* — Charles W. Stewart

(57) ABSTRACT

A process for preparing a catalyst composition comprising (a) preparing a carrier comprising (i) mordenite in an amount in the range of from 20 to 80 wt %, based on total weight of carrier, (ii) ZSM-5 type zeolite in an amount in the range of from 10 to 70 wt %, based on total weight of carrier; and (iii) an inorganic binder in an amount in the range of from 10 to 50 wt %, based on total weight of carrier; (b) incorporating in the carrier molybdenum in an amount in the range of from 1 to 10 wt %, as metal based on total weight of catalyst composition, and subjecting the thus treated carrier to a temperature of from 100 to at most 300° C. and (c) incorporating in the molybdenum containing carrier obtained in step (b) platinum in an amount of from 0.005 to 1 wt %, as metal based on total weight of catalyst composition, and subjecting the thus treated carrier to a temperature of from 200 to at most 600° C.; and a process for conversion of alkylaromatic hydrocarbons containing feedstock using a catalyst prepared by said process. Process using the prepared catalyst composition for alkylaromatic hydrocarbon conversion.

10 Claims, No Drawings

(51) Int. Cl.
*B01J 29/44* (2006.01)
*C07C 15/04* (2006.01)
*B01J 29/26* (2006.01)
*B01J 29/48* (2006.01)
*B01J 37/18* (2006.01)

(56) References Cited

U.S. PATENT DOCUMENTS

| | | | |
|---|---|---|---|
| 6,867,340 B2* | 3/2005 | Oh | B01J 29/44 585/467 |
| 2010/0029467 A1 | 2/2010 | Inui et al. | |
| 2012/0065446 A1 | 3/2012 | Boldingh | |
| 2014/0274664 A1* | 9/2014 | Weigel | B01J 29/44 502/65 |
| 2018/0361372 A1* | 12/2018 | Tammana | B01J 29/44 |
| 2020/0078777 A1* | 3/2020 | Li | B01J 35/002 |

FOREIGN PATENT DOCUMENTS

| | | |
|---|---|---|
| EP | 2046920 A1 | 4/2009 |
| WO | 2009158244 A2 | 12/2009 |

OTHER PUBLICATIONS

Baerlocher et al., "Atlas of Zeolite Framework Types", Sixth Revised Edition, 2007, 6 Pages.
Moulijn et al., "Catalysis: An Integrated Approach to Homogeneous, Heterogeneous and Industrial Catalysis", Studies in Surface Science and Catalysis, vol. 79, Chapter 10, 1993, pp. 363-400.

* cited by examiner

PROCESS FOR PREPARING A MOLYBDENUM-PLATINUM-BASED CATALYST FOR THE SYNTHESIS OF BENZENE BY TRANSALKYLATION

CROSS REFERENCE TO RELATED APPLICATIONS

This is a national stage application of International Application No. PCT/EP2017/081673, filed 06 Dec. 2017, which claims benefit of priority to European Patent Application No. 16203011.8, filed 08 Dec. 2016.

The present invention is directed to a process for preparing a catalyst composition and a process for the conversion of an alkylaromatic hydrocarbons containing feedstock using the catalyst composition.

BACKGROUND TO THE INVENTION

Reformate is an aromatic product obtained by the catalyzed conversion of straight-run hydrocarbons boiling in the 70 to 190° C. range, such as straight-run naphtha. The catalysts used for the production of reformate are often platinum-on-alumina catalysts. The reformate feedstock itself is obtained by fractionation or distillation of crude petroleum oil, its composition varying depending on the source of the crude oil, but generally having a low aromatics content. On conversion to reformate, the aromatics content is considerably increased and the resulting hydrocarbon mixture becomes highly desirable as a source of valuable chemical intermediates and as a component for gasoline. The principle components are a group of aromatics often referred to as BTX: benzene, toluene and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or btransalkylation processes have been developed to increase the proportion of para-xylene.

A further process that the gasoline producer can utilize is the hydrodealkylation of ethylbenzene to benzene.

Generally, the gasoline producer will isolate BTX from the reformate stream, and then subject the BTX stream to xylene isomerisation with the aim of maximising the para-xylene component. Xylene isomerisation is a catalytic process. Some catalysts used in this process have the ability not just to isomerise xylenes but also simultaneously to dealkylate the ethylbenzene component. Normally the para-xylene is then separated out to leave benzene, toluene (unless toluene conversion processes have already been applied), remaining mixed xylenes including ethylbenzene and aromatic compounds containing at least 9 carbon atoms. This BTX stream can be can be converted by dealkylation to selectively eliminate ethylbenzene and to increase the yield of benzene, while allowing the xylenes to reach equilibrium concentrations or can be converted by transalkylation to increase the yield of benzene and xylenes. The latter process is the subject of the present invention. In transalkylation at this latter stage of BTX treatment, it is a primary concern to ensure not just a high activity of the catalyst but also to obtain benzene of high purity.

It would be advantageous if a process for conversion of hydrocarbons, more specifically transalkylation of alkylaromatics, would produce benzene of high purity.

SUMMARY OF THE INVENTION

It is an aim to provide a process for preparing a catalyst composition which can be used in converting hydrocarbons, more specifically transalkylation of alkylaromatic hydrocarbons, preferably producing benzene of high purity.

In one aspect, the present invention is directed to a process for preparing a catalyst composition comprising (a) preparing a carrier comprising (i) mordenite in an amount in the range of from 20 to 90% by weight (wt %), based on total weight of carrier, (ii) ZSM-5 type zeolite in an amount of from 10 to 70 wt %, based on total weight of carrier; and (iii) an inorganic binder in an amount in the range of from 10 to 50 wt %, based on total weight of carrier; (b) incorporating in the carrier molybdenum in an amount in the range of from 1 to 10 wt %, as metal based on total weight of catalyst, and subjecting the thus treated carrier to a temperature of from 100 to at most 300° C. and (c) incorporating in the molybdenum containing carrier obtained in step (b) platinum in an amount of from 0.005 to 1 wt %, based on total weight of catalyst, and subjecting the thus treated carrier to a temperature of from 200 to at most 600° C.

In a further aspect, the present invention is directed at a process for conversion of feedstock containing alkylaromatic hydrocarbons using a catalyst prepared by a process as described above.

DETAILED DESCRIPTION OF THE INVENTION

It is an aim to provide a process for preparing a catalyst composition which can be used in converting alkylaromatic hydrocarbons, more specifically transalkylation of alkylaromatic hydrocarbons, preferably producing benzene of high purity. It is a further aim to provide such process having reduced gas make. It now has been found that this object can be realized when use is made of catalyst composition prepared by a particular process.

Mordenite type zeolite and ZSM-5 type zeolite are well known in the art. For the present application, these zeolites are as defined and described in "Atlas of Zeolite Framework Types," ed. Baerlocher et al., Sixth Revised Edition (Elsevier 2007).

The catalyst composition according to the present invention comprises a carrier which comprises mordenite in an amount of from 20 to 90 wt %, based on total weight of carrier. Preferably, the mordenite is present in an amount in the range of from 30 to 70 wt %, more preferably in the range of from 40 to 60 wt %, based on total weight of carrier.

The mordenite preferably has a silica to alumina molar ratio in the range of from 10 to 60. The mordenite has preferably a silica to alumina molar ratio in the range of from 10 to 40, more preferably in the range of from 10 to 30, more preferably in the range of from 15 to 25.

Preferably, the mordenite contains less than 400 ppm of transition metals, more preferably less than 300 ppm of transition metals. Transition metals are the elements of groups 3 to 12 of the IUPAC Periodic Table of the Elements. In particular, the mordenite contains less than 250 ppm of iron, more preferably less than 100 ppm of iron. Suitable mordenite has been described in EP1447131 more specifically Example 9 of EP1447131.

The mordenite preferably has a number average particle size in the range of 20 to 500 nm. Preferably, the mordenite has a number average particle size in the range of from 30 to 300 nm, more preferably in the range of from 50 to 200 nm.

The average particle size of the zeolites described herein is determined by calculating the number average particle size of a sample which has been measured by using X-ray diffraction (line broadening) and the Scherrer equation. This technique is well known in the art for determining crystallite particle size (see, for example, "Catalysis: An Integrated Approach to Homogeneous, Heterogeneous and Industrial Catalysis", J. A. Moulijn, P. W. N. M. van Leeuwen, R. A. van Santen (Eds.), Elsevier, 1993, pp. 365-367, WO 2009/158244 A2).

Specifically, the mean crystallite length parallel to the direction of the 12-ring channels in the mordenite is to be measured by applying the Scherrer equation to x-ray diffraction data, wherein prior to analysis, the mordenite is converted to the hydrogen form by heating the NH4-exchanged form to 540° C. for 2 hours in nitrogen and then for 5 hours in air. Specifically, the full width at half maximum (FWHM) is to be measured for the (002) diffraction peak at 23.8° 2θ for CuKα radiation and then the mean crystallite length, L0002, parallel to the direction of the 12-ring channels may be calculated from the Scherrer equation. It is assumed that the peaks are partially Gaussian and partly Cauchy in shape.

The present catalyst composition comprises a carrier which comprises a ZSM-5 type zeolite in an amount of 10 to 70 wt %, based on total weight of carrier. Preferably, the ZSM-5 type zeolite is present in an amount in the range of from 15 to 60 wt %, more preferably in the range of from 20 to 40 wt %, based on total weight of carrier.

The ZSM-5 type zeolite preferably has a silica to alumina molar ratio in the range of from 10 to 50, preferably in the range of 15 to 40, more preferably in the range of from 15 to 35, and more preferably in the range of from 18 to 30.

The ZSM-5 type zeolite preferably has a number average particle size in the range of 20 to 500 nm. Preferably, the ZSM-5 type zeolite has a number average particle size in the range of from 30 to 300 nm, more preferably in the range of from 50 to 200 nm. It was observed that a low number average particle size of the ZSM-5 type zeolite used in accordance with the present invention can improve the benzene purity. The average particle size is determined as hereinbefore described by using X-ray diffraction (line broadening) and the Scherrer equation. Suitable ZSM-5 type zeolites to be used in accordance with the present invention can be prepared as for example described in U.S. Pat. Nos. 3,702,886 and 4,511,547. Suitable examples of ZSM-5 type zeolites include CBV 3014E, CBV 3020E and CBV 8014, available commercially from Zeolyst International.

The catalyst composition contains an inorganic binder in an amount in the range of from 10 to 50 wt %, based on total weight of carrier. Preferably, the inorganic binder is present in an amount in the range of from 10 to 40 wt %, more preferably in the range of from 15 to 30 wt %, based on total carrier.

Suitably, the inorganic binder is selected from the group consisting of gamma-alumina, silica, silica-alumina, bentonite, kaolin, titania, zirconia, ceria, gallia, clinoptilolite, montmorillonite, and any mixture thereof. Preferred inorganic binder is alumina, more specifically gamma alumina.

In shaped form, for example as extrudates, the carrier generally has a BET surface area falling in the range of from 200 to 600 m2/g, preferably 250 to 500 m2/g, more preferably from 350 to 450 m2/g. The BET surface area suitably is measured according to ASTM D3663-03(2015). Furthermore, the extrudates preferably have a pore volume, by mercury intrusion, in the range of from 0.2 to 1.2 ml/g, preferably 0.4 to 1.0 ml/g, more preferably 0.5 to 0.8 ml/g. Pore volume is measured according to ASTM D4222-03.

The present catalyst composition may be shaped in any particular form. Suitable shapes include trilobes and cylinders, Preferably, the present catalyst composition is in the shape of trilobes.

The carrier can be prepared by mixing the mordenite, the ZSM-5 type zeolite and the inorganic binder, shaping the mixture and subjecting the shaped mixture to calcination at a temperature of from 200 to 800° C. The shaped mixture can be dried before calcination. Drying temperatures can suitably be in the range of from 50 to 200° C. Drying times can suitably be in the range of from 0.5 to 24 hours. Calcination temperatures can suitably be in the range of from 200 to 800° C., preferably in the range of from 300 to 600° C. In the calcination of the carrier material, a relatively short time can suitably be applied such as in the range of from 0.5 to 5 hours. The calcination can suitably be carried out at a temperature in the range of from 400 to 700° C., preferably in the range of from 450 to 600° C.

The present catalyst composition comprises molybdenum in an amount in the range of from 1 to 10 wt %, as metal based on total weight of catalyst composition, more preferably in the range of from 2 to 9 wt %, more preferably of from 2 to 8 wt %, more preferably of from 2 to 6 wt % of metal based on total weight of catalyst composition.

The present catalyst further comprises platinum in an amount in the range of from 0.005 to 1 wt %, as metal based on total weight of catalyst composition, more preferably in the range of from 0.01 to 0.5 wt %, more specifically of from 0.01 to 0.2 wt %. Most preferably, the present catalyst further comprises platinum in an amount in the range of from 0.01 to 0.1 wt % or 0.01 to 0.05 wt %, as metal based on total weight of catalyst composition The amounts of metal are calculated as metal independent from the actual compound present.

The catalyst composition according to the invention can suitably have such shape that a reactor filled with the catalyst particles has an average void fraction of at least 10% by volume, preferably in the range of from 20 to 70%, more preferably in the range of from 35 to 55% by volume.

The molybdenum and the platinum suitably are incorporated in the carrier with the help of a separate metal salt solutions. Preferably, each molybdenum and platinum are incorporated by pore volume impregnation.

The molybdenum can be incorporated with the help of a solution comprising heptamolybdate.

The platinum can be incorporated with the help of a solution comprising one or more compounds selected from the group consisting of chloroplatinic acid and ammonium stabilised platinum salts.

After incorporating molybdenum in the carrier, the molybdenum containing carrier is subjected to a heat treatment. The heat treatment of step (b) is of from 100 to at most 300° C., preferably of from 100 to at most 250° C., more preferably at most 200° C., most preferably at most 170° C.

It is especially preferred that the temperature of the molybdenum containing carrier obtained in step (b) is at most 170° C. in step (c) until platinum has been incorporated in the molybdenum containing carrier in step (c). The thus treated carrier is then subjected to a heat treatment.

The heat treatment of step (c) is of from 200 to at most 600° C., preferably at least 300° C., more preferably at least 350° C., more preferably at least 400° C. and preferably at most 570° C., more preferably at most 550° C. and most preferably at most 520° C.

The heat treatment of each step (b) and (c) can suitably be applied for a time period in the range of from 0.5 to 5 hours, more specifically of from 1 to 4 hours, more preferably of from 1 to 3 hours.

Before use of the catalyst composition as a catalyst, it will be preferred that the metals on the catalyst composition are in metallic (and not oxidic) form. Accordingly, the catalyst composition preferably is subjected to reducing conditions, which are, for example, heating in a reducing atmosphere, such as in hydrogen optionally diluted by an inert gas, such as nitrogen or carbon dioxide, at temperature in the range of from 150 to 600° C. for a period of time in the range from 0.5 to 5 hours.

The present invention also relates to a process for the conversion, more specifically transalkylation, of an alkylaromatic hydrocarbons containing feedstock using a catalyst prepared in accordance with the present invention.

In a preferred embodiment, the present invention provides a process for the transalkylation of an alkylaromatic hydrocarbon feedstock comprising toluene and alkylaromatic hydrocarbons containing at least 9 carbon atoms.

Suitably, the alkylaromatic hydrocarbon feedstock comprises at least 90 wt % of the total amount of toluene and alkylaromatic hydrocarbons containing at least 9 carbon atoms. Most preferably, the alkylaromatic hydrocarbon feedstock comprises of from 35 to 75 wt % of toluene and of from 25 to 65 wt % of alkylaromatic compounds containing at least 9 carbon atoms. The alkylaromatic hydrocarbons preferably consist of hydrogen, carbon and optionally oxygen.

The feedstock suitably is contacted with the catalyst in the presence of hydrogen. The contacting may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The present transalkylation process preferably is carried out at a temperature in the range of from 200 to 600° C., preferably in the range of from 250 to 500° C., and more preferably in the range of from 300 to 400 C°.

The process preferably is carried out at a pressure in the range of from 1 to 30 barg, preferably at a pressure in the range of from 2 to 20 barg, and more preferably at a pressure in the range of from 2 to 10 barg.

The weight space velocity applied in the process is suitably in the range of from 0.2 to 30 hr-1, preferably from 2 to 20 hr-1, and more preferably in the range of from 3 to 6 hr-1.

The feed to hydrogen ratio mol·mol-1 is in the range of from 0.5 to 100, preferably in the range of from 1 to 10.

The reaction effluent preferably will be recovered and subjected to a distillation treatment to remove the desired products, i.e., xylene and benzene. Unreacted reactant such as for instance toluene can suitably be recycled for further reaction.

The present disclosure is not limited to the embodiments as described above and the appended claims. Many modifications are conceivable and features of respective embodiments may be combined.

The following examples of certain aspects of some embodiments are given to facilitate a better understanding of the present invention. In no way should these examples be read to limit, or define, the scope of the invention.

EXAMPLES

Example 1

A carrier was prepared by extruding a mixture comprising, based on dry components, 50 wt % of a mordenite having silica to alumina molar ratio of 20 and a number average crystal size between 60 and 100 nm, 30 wt % of ZSM-5 zeolite having a silica to alumina molar ratio of 23 and a number average crystal size of 100 nm and 20 wt % of alumina (Pural SB1 obtainable from Sasol). The green extrudates were dried and calcined at about 550° C. for 1 hour.

This carrier was used in the preparation of all catalysts described hereinbelow.

Metal was incorporated into the carrier by pore volume impregnation.

Molybdenum was incorporated with the help of an aqueous solution of ammonium heptamolybdate.

Platinum was incorporated with the help of an aqueous solution of chloroplatinic acid.

The concentration of each molybdenum and platinum was such as to provide a final catalyst having a platinum content of 0.03 wt % and/or 4 wt % of molybdenum, each metal based on total catalyst. After each impregnation was completed, the catalyst was subjected to a heat treatment of 140 or 480° C. during 2 hours with a sufficient low ramping rate to achieve adequate dispersion of the metallic phase. Full information on the preparation of each comparative catalysts A-F and Catalyst 1 (prepared in accordance with the process of the present invention), the order of impregnation and the temperature of heat treatment after impregnation is provided in Table 2.

Example 2

Comparative catalysts A-Fand Catalyst 1 prepared in accordance with the process of the present invention were used in transalkylation of an alkylaromatics feed as described in Table 1.

TABLE 1

| Component | Content (wt %) |
|---|---|
| Toluene (C7) | 50.4 |
| Trimethylbenzenes (C9) | 28.6 |
| Ethyltoluenes (C9) | 11.0 |
| Propylbenzenes (C9) | 0.8 |
| Indane (C9) | 1.4 |
| Ethyl-xylenes (C10) | 7.0 |
| Tetramethylbenzenes (C10) | 0.5 |
| C10+ rest | 0.3 |

The product obtained was evaluated using gas chromatography. The testing was carried out at a total pressure of 30 barg and a hydrogen:hydrocarbon molar ratio of 5. These conditions were maintained throughout the experiment.

Prior to the test, the catalysts were dried in a flow of hydrogen at room temperature and atmospheric pressure for 1 hour, then heated to 400° C. for 1 hour, pressurized to 30 barg, maintained under these conditions for a further 1 hour, and finally cooled to 360° C. The feed was introduced at a weight hourly space velocity of 2.5 h-1.

For catalyst aging, the temperature was increased to 420° C. and maintained at that temperature for 24 hours. Subsequently, the reactor was cooled to 360° C. and the weight hourly space velocity was increased to 3.5 h-1. Catalysts were evaluated under these conditions at temperatures in the 320 to 380° C. range.

The temperature required to reach a total conversion of toluene and C9+ aromatics to the desired C8-aromatics (C8A) and benzene of 45% was determined by interpolation of the conversions at different temperatures. The key performance parameters at this temperature are compared in Table 2.

EB/C8A represents the percentage of ethylbenzene (EB) in the C8 aromatics (C8A) fraction. Benzene purity is defined as the percentage of benzene in the mixture of benzene and its coboilers (cyclohexane and methylcyclopentane). Trimethylbenzene (TMB) conversion is the percent of all trimethylbenzenes converted by the catalyst. The total gasmake is defined as the weight percentage of C1-C5 molecules in the reactor effluent.

Surprisingly, in the present invention it has been found that depending on the sequence of metal dopant addition and the temperature employed for intermediate and final heat-treatments, strikingly different results are obtained in subsequent catalytic testing. In particualar, only for Catalyst 1, prepared by first impregnating molybdenum on the ZSM-5/mordenite carrier, drying at a low temperature of 140° C., and then directly following with impregnation with platinum, is an excellent high benzene purity is obtained, while also maintaining an excellent activity. Other sequences, used to produce catalysts comparative Catalysts D-F, either lead to behaviour similar to the Pt-only (comparative Catalyst C) or Mo-only catalysts (comparative Catalyst B), all unattractive in commercial operation.

It will be clear from Table 2 that a catalyst prepared according to the invention unexectedly allows to obtain a high conversion of toluene and aromatic compounds containing at least 9 carbon atoms while obtaining benzene of

TABLE 2

Catalyst overview and performances in transalkylation

|  | Comparative | | | | | | |
| --- | --- | --- | --- | --- | --- | --- | --- |
|  | Catalyst A | Catalyst B | Catalyst C | Catalyst D | Catalyst E | Catalyst F | Catalyst 1 |
| CARRIER | | | | | | | |
| Mordenite (wt %) | 50 | 50 | 50 | 50 | 50 | 50 | 50 |
| ZSM-5 (wt %) | 30 | 30 | 30 | 30 | 30 | 30 | 30 |
| Alumina (wt %) | 20 | 20 | 20 | 20 | 20 | 20 | 20 |
| DOPANTS | | | | | | | |
| 1st metal, (wt %)** | Mo (4) | Mo (4) | Pt (0.03) | Mo (4) | Pt (0.03) | Pt (0.03) | Mo (4) |
| 1st heat treatment (° C.) | 140 | 480 | 480 | 480 | 480 | 480 | 140 |
| 2nd metal, (wt %)** | — | — | — | Pt (0.03) | Mo (4) | Mo (4) | Pt (0.03) |
| 2nd heat treatment (° C.) | — | — | — | 480 | 140 | 480 | 480 |
| CATALYST PERFORMANCE | | | | | | | |
| Total conversion (%) | 45 | 45 | 45 | 45 | 45 | 45 | 45 |
| Temperaturerequired (° C.) | 396 | 359 | 347 | 344 | 368 | 350 | 348 |
| Xylene yield (wt %) | 31.7 | 31.3 | 28.4 | 30.6 | 30.5 | 30.6 | 31.4 |
| Benzene + xylene selectivity (%) | 83.8 | 85.5 | 76.3 | 82.0 | 81.6 | 82.4 | 85.6 |
| Benzene Purity (%) | 99.04 | 99.85 | 95.89 | 95.91 | 95.62 | 96.34 | 99.34 |
| MEB Conversion (%) | 100.00 | 82.22 | 79.74 | 89.85 | 96.37 | 93.23 | 86.25 |
| TMB Conversion (%) | 56.04 | 52.74 | 48.27 | 51.06 | 51.48 | 50.47 | 51.64 |
| EB in C8A (%) | 0.00 | 2.46 | 2.85 | 1.42 | 0.65 | 1.00 | 1.94 |
| Aromatic losses (mol %) | 0.89 | 0.96 | 6.47 | 2.95 | 3.08 | 2.71 | 1.12 |
| Total gasmake (%) | 6.48 | 5.48 | 9.04 | 7.02 | 7.54 | 7.05 | 5.72 |

*wt % based on total carrier.
**wt % based on total catalyst.

In Table 2, comparative Catalysts A and B comprise a ZSM-5/mordenite carrier in conjunction with molybdenum as the sole dopant. Said catalysts are treated at different temperatures. Both systems show high benzene purity, but the activity, as expressed by the temperature required to reach 45% total conversion, of both systems is insufficient for effective commercial application.

Comparative Catalyst C is based on platinum as the only dopant on a ZSM-5/mordenite carrier. Unlike comparative Catalysts A and B, Comparative Catalyst C shows satisfactory activity (as denoted by a lower required temperature to acheive 45% total conversion). However, said catalyst displays an unacceptably low benzene purity.

Comparative Catalysts D-F and Catalyst 1 are all catalysts comprising a ZSM-5/mordenite carrier in conjunction with a combination of molybdenum and platinum dopants. However, said catalysts are prepared by different methods.

high purity. A further advantage is that the benzene of high purity can be obtained with a low total gas make.

Of the catalysts tested in Table 2, only Catalyst 1, which was prepared by the process of the present invention, is capable of providing high benzene purity, high benzene yield, and high product selectivity at commercially viable reaction temperatures. Comparative catalysts A-F either have too low an activity or too low a selectivity for utility in industrial processes.

That which is claimed is:

1. A process for preparing a catalyst composition comprising:
    (a) preparing a carrier comprising (i) mordenite in an amount in the range of from 20 to 80 wt %, based on total weight of carrier, (ii) ZSM-5 type zeolite in an amount in the range of from 10 to 70 wt %, based on total weight of carrier; and (iii) an inorganic binder in an amount in the range of from 10 to 50 wt %, based on total weight of carrier;

(b) incorporating in the carrier molybdenum in an amount in the range of from 1 to 10 wt %, as metal based on total weight of catalyst composition, and subjecting the thus treated carrier to a temperature of from 100 to at most 300° C.; and (c) incorporating in the molybdenum containing carrier obtained in step (b) platinum in an amount of from 0.005 to 1 wt %, as metal based on total weight of catalyst composition, and subjecting the thus treated carrier to a temperature of from 200 to at most 600° C.

2. The process according to claim 1, wherein step (b) comprises subjecting the molybdenum containing carrier to a temperature of from 100 to at most 170° C.

3. The process according to claim 2, wherein the temperature of the molybdenum containing carrier in step (c) is at most 170° C. until platinum has been incorporated in the molybdenum containing carrier in step (c) and the thus treated carrier is then subjected to a temperature of from 200 to at most 600° C.

4. The process according to claim 1, wherein the mordenite has a silica to alumina molar ratio in the range of from 10 to 40.

5. The process according to claim 1, wherein the ZSM-5 type zeolite has a silica to alumina molar ratio in the range of from 15 to 40.

6. The process according to claim 1, wherein the ZSM-5 type zeolite has a number average particle size in the range of from 20 to 500 nm, as determined by X-ray diffraction.

7. The process according to claim 1, wherein the mordenite has a number average particle size in the range of from 20 to 500 nm, as determined by X-ray diffraction.

8. The process according to claim 1, wherein the carrier is prepared by mixing the mordenite, the ZSM-5 type zeolite and the inorganic binder, shaping the mixture and subjecting the shaped mixture to a temperature of from 200 to 800° C.

9. A process for the conversion of a feedstock containing alkylaromatic hydrocarbons, wherein the process comprises: contacting the feedstock with using a catalyst prepared by a process according to claim 1 in the presence of hydrogen; and yielding a reaction effluent.

10. The process according to claim 9, wherein the feedstock comprises of from 35 to 75 wt % of toluene and of from 25 to 65 wt % of alkylaromatic compounds containing at least 9 carbon atoms, all amounts based on total amount of feedstock.

* * * * *